United States Patent [19]

Hashimoto et al.

[11] Patent Number: 5,580,765

[45] Date of Patent: *Dec. 3, 1996

[54] PROCESS FOR PRODUCING OPTICALLY ACTIVE A-HYDROXYCARBOXYLIC ACID HAVING PHENYL GROUP USING GORDONA TERRAE

[75] Inventors: Yoshihiro Hashimoto; Takakazu Endo; Koji Tamura; Yuji Hirata, all of Kanagawa, Japan

[73] Assignee: Nitto Chemical Industry Co., Ltd., Tokyo, Japan

[*] Notice: The term of this patent shall not extend beyond the expiration date of Pat. No. 5,326,702.

[21] Appl. No.: 191,164

[22] Filed: Feb. 3, 1994

[30] Foreign Application Priority Data

Feb. 3, 1993 [JP] Japan .................................. 5-037275

[51] Int. Cl.$^6$ ..................................................... C12P 7/42
[52] U.S. Cl. .......................... 435/146; 435/280; 435/822
[58] Field of Search .................................. 435/146, 280, 435/822

[56] References Cited

U.S. PATENT DOCUMENTS 5,223,416  6/1993  Endo et al. .............................. 435/128
5,283,193  2/1994  Yamamoto et al. ..................... 435/280
5,326,702  7/1994  Endo et al. .............................. 435/129

FOREIGN PATENT DOCUMENTS 0348901  1/1990  European Pat. Off. .......... C12P 7/40
0449648  10/1991  European Pat. Off. ..
0486289  5/1992  European Pat. Off. ..

OTHER PUBLICATIONS

ATCC Catalogue of Bacteria and Bacteriophages p. 157 (1992).
*Applied and Environmental Microbiology*, vol. 57, No. 10 pp. 3028–3032 (1991).

Primary Examiner—Michael G. Wityshyn
Assistant Examiner—S. Saucier
Attorney, Agent, or Firm—Sughrue, Mion, Zinn, Macpeak & Seas

[57] ABSTRACT

A biological process for predominantly producing an optically active α-hydroxycarboxylic acid having a phenyl group directly from a racemic α-hydroxynitrile or a mixture of an aldehyde corresponding to the nitrile and prussic acid as a substrate is disclosed, comprising reacting a microorganism belonging to the genus Gordona with the substrate in a neutral to basic aqueous medium. A desired optically active α-hydroxycarboxylic acid having a phenyl group can be obtained quantitatively at a high optical purity.

6 Claims, No Drawings

PROCESS FOR PRODUCING OPTICALLY ACTIVE A-HYDROXYCARBOXYLIC ACID HAVING PHENYL GROUP USING *GORDONA TERRAE*

FIELD OF THE INVENTION

This invention relates to a biological process for producing an optically active α-hydroxycarboxylic acid having a phenyl group. More particularly, it relates to a process for producing an optically active α-hydroxycarboxylic acid having a phenyl group as represented by formula (I) shown below, by the action of a microorganism capable of asymmetrically hydrolyzing a nitrile group of a racemic α-hydroxynitrile represented by formula (II) shown below. The optically active α-hydroxycarboxylic acid of formula (I) is of industrial importance as a starting material for synthesizing pharmaceuticals and agrochemicals, such as antibiotics or drugs acting on the sympathetic nervous system, and as a resolving reagent.

BACKGROUND OF THE INVENTION

Known processes for producing an optically active α-hydroxycarboxylic acid having a phenyl group include optical resolution of racemates by crystallization or chromatography and asymmetric synthesis through organochemical procedures. These processes generally involve complicated operations, only to attain a low yield of a product.

To overcome these problems, biological processes utilizing microorganisms have been proposed. For example, it has been proposed to asymmetrically hydrolyze substituted or unsubstituted mandelonitrile or substituted or unsubstituted mandelamide by the action of a microorganism belonging to the genus Alcaligenes, Pseudomonas, Rhodopseudomonas, Corynebacterium, Acinetobacter, Bacillus, Mycobacterium, Rhodococcus or Candida to obtain optically active mandelic acid or derivatives thereof as disclosed in European Patent Publication No. 0 348 901 A (corresponding to JP-A-2-84198 (the term "JP-A" as used herein means an "unexamined published Japanese patent application")) and *Applied and Environmental Microbiology*, Vol. 57, pp. 3028–3032 (1991). It is also known to obtain a predominant proportion of R(−)-mandelic acid or a derivative thereof directly from racemic mandelonitrile or a derivative thereof by the action of a microorganism belonging to the genus Pseudomonas, Alcaligenes, Acinetobacter, Caseobacter, Nocardia, Bacillus, Brevibacterium or Aureobacterium, as disclosed in U.S. Pat. No. 5,223,416 (corresponding to JP-A-4-218385, JP-A-4-99495 and JP-A-4-99496).

In these biological processes, discovery of a new microorganism with higher activity and higher optical selectivity would produce a great industrial benefit.

SUMMARY OF THE INVENTION

The present inventors searched extensively for a microorganism capable of producing an optically active α-hydroxycarboxylic acid having a phenyl group with industrial advantages. They found that a novel microorganism belonging to the genus Gordona isolated from soil is effective.

The present invention relates to a process for predominantly producing an optically active α-hydroxycarboxylic acid having a phenyl group as represented by formula (I):

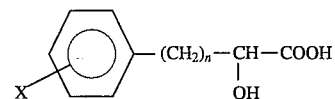

wherein X represents a hydrogen atom, a hydroxyl group, an aliphatic saturated alkyl group having from 1 to 3 carbon atoms, an aliphatic saturated alkoxy group having from 1 to 3 carbon atoms, a thioalkyl group, a halogen atom, a phenyl group, a phenoxy group, an amino group or a nitro group, which is bonded to the o-, m-, or p-position; and n represents 0, 1 or 2, which comprises reacting a microorganism capable of asymmetrically hydrolyzing a nitrile group of a racemic α-hydroxynitrile represented by formula (II):

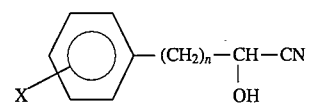

wherein X and n are as defined above, and wherein said microorganism belongs to the genus Gordona or treated cells thereof, with a racemic α-hydroxynitrile represented by formula (II) or a mixture of an aldehyde corresponding to said nitrile and prussic acid in a neutral to basic aqueous medium.

The present invention is based on the fact that the α-hydroxynitrile of formula (II) is easily racemized in a neutral to basic aqueous medium at the dissociation equilibrium between the α-hydroxynitrile and the corresponding aldehyde and prussic acid. The inventors found that the α-hydroxynitrile of formula (II) can be directly converted to an optically active α-hydroxycarboxylic acid having a phenyl group represented by formula (I) with predominance over a D-form or an L-form by coupling the above-mentioned racemization reaction system with the above-mentioned microorganism. The term "with predominance" as used herein means that a D-form or an L-form is obtained from a racemic compound in a yield of from 50 to 100% based on the amount of reactant according to formula (II).

DETAILED DESCRIPTION OF THE INVENTION

The microorganism which can be used in the present invention belongs to the genus Gordona and is capable of asymmetrically hydrolyzing a nitrile group of a racemic α-hydroxynitrile of formula (II) to produce and accumulate in a high concentration an optically active α-hydroxycarboxylic acid having a phenyl group represented by formula (I).

The microorganism typically includes *Gordona terrae* MA-1 which the inventors isolated from soil and deposited with National Institute of Bioscience & Human Technology (formerly, Fermentation Research Institute), Agency of Industrial Science & Technology under deposit receipt number FERM BP-4535. Morphological and physiological properties of this strain are described below.

| MA-1: | |
|---|---|
| Shape: | polymorphic bacillus |
| Gram's stain: | + |
| Spore: | − |
| Motility: | − |
| Oxidase: | − |
| Catalase: | + |
| Color of colony: | pink to orange |
| Rod-coccus cycle: | + |

MA-1:

| | |
|---|---|
| Extension of peripheral cells of colony: | observed |
| Formation of aerial hypha | not observed |
| Behavior toward oxygen | aerobic |
| Diamino acid of cell wall: | meso-diaminopimelic acid |
| Glycolyl test: | + (glycolyl type) |
| Sugar composition of cell wall: | |
| Arabinose: | + |
| Galactose: | + |
| Existence of quinone: | MK-9 (H$_2$) |
| Adenine decomposition: | − |
| Tyrosine decomposition: | − |
| Urea decomposition: | + |
| Utilizability: | |
| Inositol | − |
| Maltose | − |
| Mannitol | + |
| Rhamnose | + |
| Sorbitol | + |
| Sodium m-hydroxybenzoate | − |
| Sodium benzoate | + |
| Sodium citrate | + |
| Sodium lactate | + |
| Testosterone | + |
| Acetamide | − |
| Sodium pyruvate | + |
| Growth in the presence of 0.02% sodium azide | + |
| Growth at 10° C. | + |
| Growth at 40° C. | + |
| Growth in the presence of 0.001% Crystal Violet | + |
| Growth in the presence of 0.3% phenylethanol | + |
| Growth in the presence of 5% NaCl | + |
| Growth in the presence of 7% NaCl | + |

The above-described taxonomical properties were examined by referring to *Bergey's Manual of Systematic Bacteriology* (1986), *J. Gen. Appl. Microbiol.*, Vol. 34, pp. 341–348 (1988), and *Int. J. Syst. Bacteriol.*, Vol. 39, p. 371 (1989). MA-1 strain was identified as belonging to *Gordona terrae*. Specific examples of the compounds of formula (II) which can be used as a substrate in the present invention include mandelonitrile, 2-chloromandelonitrile, 3-chloromandelonitrile, 4-chloromandelonitrile, 4-hydroxymandelonitrile, 4-methylmandelonitrile, 4-methoxymandelonitrile, 4-methylthiomandelonitrile, 4-aminomandelonitrile, 4-nitromandelonitrile, 4-aminomandelonitrile, 4-nitromandelonitile, 3-phenoxymandelonitrile, phenyllactonitrile, 4-phenyl-α-hydroxybutyronitrile, 3-(2-methoxyphenyl)-lactonitrile, 3-(3-methoxyphenyl)-lactonitrile, 3-(4-methoxyphenyl)-lactonitrile, 4-(4-fluorophenyl)-α-hydroxybutyronitrile, 4-(2-chlorophenyl)-α-hydroxybutyronitrile, 4-(4-bromophenyl)-α-hydroxybutyronitrile, 4-(2-trifluoromethylphenyl)-α-hydroxybutyronitrile, 4-(3-trifluoromethylphenyl)-α-hydroxybutyronitrile and 4-(2-hydroxyphenyl)-α-hydroxybutyronitrile.

Cultivation of the microorganism is carried out by using usual media containing assimilable carbon sources (e.g., glycerol, glucose, saccharose, malt extract, lactose, and fructose); assimilable nitrogen sources (e.g., casamino acid, meat extract, and yeast extract); and inorganic nutrients essential for growth (e.g., magnesium chloride, sodium sulfate, calcium chloride, manganese sulfate, iron chloride, and zinc sulfate).

To obtain increased enzyme activity, an enzyme inducer preferably is added to the culture medium in the initial or middle stage of cultivation in such a concentration as not to significantly inhibit growth. Suitable enzyme inducers include nitriles (e.g., cinnamonitrile, benzyl cyanide, isobutyronitrile, β-phenylpropionitrile, benzonitrile, 2-, 3- or 4-cyanopyridine, 1-cyclohexenylacetonitrile, ε-caprolactam, γ-butyronitrile, and o-aminobenzonitrile); and amides (e.g., isobutylamide, phenylacetamide, and 4-pyridinecarboxylic acid amide).

Culturing is aerobically conducted at a pH from 4 to 10 and a temperature from 5° to 50° C., for a period of about 1 to 7 days, until the maximum activity is reached.

The asymmetric hydrolysis reaction can be carried out by suspending microbial cells harvested from the culture or treated microbial cells (e.g., dried cells, ruptured cells, a crude or purified isolated enzyme, immobilized microbial cells or an immobilized enzyme) in an aqueous medium (e.g., water and a buffer solution), and bringing a racemic α-hydroxynitrile of formula (II) or a mixture of an aldehyde corresponding to the nitrile and prussic acid in contact with the cell suspension. The reaction system should be maintained nearly neutral or basic in order to racemize the α-hydroxynitrile of formula (II). That is, the pH of the reaction system should be kept within a range of 4 to 11, and preferably 6.5 to 10.

The concentration of the substrate in the reaction system usually ranges from 0.1 to 10% by weight, and preferably 0.2 to 5.0% by weight in terms of the racemic α-hydroxynitrile of formula (II) based on the total reaction system, while varying depending on the sensitivity of the enzyme to the aldehyde corresponding to the racemic α-hydroxynitrile of formula (II) or prussic acid.

To reduce enzyme denaturation by an aldehyde, sodium sulfite, acid sodium sulfite, sodium dithionite, potassium sulfite, acid potassium sulfite, potassium dithionite, ammonium sulfite, acid ammonium sulfite, and ammonium dithionite in an amount of 1 to 1000 mM may be added.

The microorganism usually is used in an amount of 0.01 to 5.0% by weight on a dry basis based on the substrate. The reaction is usually conducted at a temperature of 0° to 50° C., and preferably 10° to 30° C., for a period of 0.1 to 100 hours.

The reaction product, i.e., an optically active α-hydroxycarboxylic acid of formula (I), can be isolated from the reaction mixture by known procedures. For example, the microbial cells may be removed by centrifugation, and if desired, granular components, proteins, and polysaccharides may be removed by ultrafiltration or the like. If desired, the supernatant may be treated with activated carbon. Then, the supernatant may be concentrated under reduced pressure or extracted with an organic solvent in an acidic condition, followed by repeated recrystallization from benzene, etc., to obtain a high purity crystal.

The present invention provides an industrially excellent process for preparing an optically active α-hydroxycarboxylic acid having a phenyl group represented by formula (I) at almost quantitative selectivity and at high optical purity.

The present invention will now be illustrated in greater detail with reference to Examples, but it should be understood that the present invention is not deemed to be limited thereto. All percentages are by weight unless otherwise indicated.

EXAMPLE 1

Preparation of L-3-Phenyllactic Acid (1) Culturing:

*Gordona terrae* MA-1 (FERM BP-4535) was aerobically cultured in a medium having the following composition, with 0.05% benzyl cyanide added as an inducer, at 30° C. for 72 hours.

| Medium Composition: | |
|---|---|
| Glycerolt | 20 g |
| Yeast extract | 3 g |
| Potassium primary phosphate | 6.8 g |
| Sodium secondary phosphate | 7.1 g |
| Sodium sulfate | 2.8 g |
| Magnesium chloride | 0.4 g |
| Calcium chloride | 0.04 g |
| Manganese sulfate | 0.03 g |
| Iron chloride | 0.006 g |
| Zinc sulfate | 0.003 g |
| Distilled water | 1000 ml |
| pH = 7.5 | |

(2) Asymmetric Hydrolysis:

Microbial cells harvested from the culture were washed with a 50 mM phosphoric acid buffer solution (pH=8.2) by centrifugation and suspended in the same buffer solution containing 10 mM phenyllactonitrile at such a cell concentration as to have optical density of 20 at 630 nm ($OD_{630}$). The cell suspension was allowed to react at 30° C. for 96 hours while shaking.

After completion of the reaction, the microbial cells were removed by centrifugation. The content of phenyllactic acid in the supernatant was determined by liquid chromatography (column: Wakosil ODS 5C18; carrier solution: 0.1M phosphoric acid:acetonitrile=3:1 by volume; monitor: 254 nm). The supernatant was adjusted to pH 12 with 6N NaOH and extracted twice with an equal amount of ethyl acetate to remove any unreacted phenyllactonitrile. The aqueous layer was adjusted to pH 1.2 with sulfuric acid and extracted twice with an equal amount of ethyl acetate. The extract was evaporated to dryness in an evaporator. The residue was dissolved in water and analyzed on an optical resolution column (MCI gel CRS-10 W; carrier solution: 2 mM $CuSO_4 \cdot 5H_2O$:acetonitrile=85:15 by volume). The results obtained are shown below.

3-Phenyllactic Acid:
  Yield: 6.5 mM (65%)
  Optical Purity: 60% ee (L-form)

EXAMPLE 2

Preparation of L-3-Phenyllactic Acid

Microbial cells harvested in the same manner as in Example 1 were suspended in a phosphoric acid buffer solution (pH=8.2) containing 10 mM phenylaldehyde and 10 mM potassium cyanide to a cell concentration of $OD_{630}$=20. The cell suspension was allowed to react at 30° C. for 96 hours with shaking.

The reaction mixture was worked-up in the same manner as in Example 1. The phenyllactic acid content and its optical purity were determined in the same manner as in Example 1. The results of analyses are shown below.

3-Phenyllactic Acid:
  Yield: 7.5 mM (75%)
  Optical Purity: 63% ee (L-form)

EXAMPLE 3

Preparation of L-4-Phenyl-α-hydroxybutyric Acid

Microbial cells harvested in the same manner as in Example 1 were suspended in a phosphoric acid buffer solution (pH=8.2) containing 10 mM 4-phenyl-α-hydroxybutyronitrile to a concentration of $OD_{630}$=20. The cell suspension was allowed to react at 30° C. for 96 hours with shaking. Further, the same reaction was carried out in the presence of 100 mM sodium sulfite for reducing enzyme denaturation by the aldehyde.

The reaction mixture was worked-up in the same manner as in Example 1. The 4-phenyl-α-hydroxybutyric acid content and the optical purity were determined in the same manner as in Example 1. The results of analyses are shown in Table 1 below.

TABLE 1

| Sodium Sulfite | Yield (mM) | Optical Purity (L-Form) (% ee) |
|---|---|---|
| not added | 7.0 (70%) | 90 |
| added | 9.0 (90%) | 92 |

EXAMPLE 4

Preparation of D-Mandelic Acid

Microbial cells harvested from the culture in the same manner as in Example 1 were suspended in a phosphoric acid buffer solution (pH=8.2) containing 10 mM mandelonitrile to a cell concentration of $OD_{630}$=20. The cell suspension was allowed to react at 30° C. for 24 hours with shaking.

The reaction mixture was worked-up in the same manner as in Example 1. The mandelic acid content and optical purity were determined in the same manner as in Example 1. The results of analyses are shown below.

D-Mandelic Acid:
  Yield: 9.8 mM (98%)
  Optical Purity: 98% ee (D-form)

EXAMPLE 5

Preparation of D-Mandelic Acid and Derivatives Thereof

Microbial cells harvested from the culture in the same manner as in Example 1 were suspended in a phosphoric acid buffer solution (pH=8.2) containing each of the substrates shown in Table 2 below to prepare a cell suspension ($OD_{630}$=10 to 30). The cell suspension was allowed to react at 30° C. for the time shown in Table 2, while shaking. After the reaction, the microbial cells were removed by centrifugation. The content and optical purity of mandelic acid or a mandelic acid derivative accumulated in the supernatant were determined in the same manner as in Example 1. The results obtained are shown in Table 2.

TABLE 2

| Substrate | Amount of Substrate (mM) | Reaction Time (hr) | Yield (mM) | Optical Purity (D-Form) (% ee) |
|---|---|---|---|---|
| Benzaldehyde + prussic acid | 10 | 2 | 9.8 (98%) | 100 |
| 2-Chloromandelonitrile | 7 | 17 | 6.8 (97%) | 100 |
| 3-Chloromandelonitrile | 6 | 17 | 4.6 (97%) | 100 |
| 4-Chloromandelonitrile | 7 | 17 | 4.5 (64%) | 100 |

TABLE 2-continued

| Substrate | Amount of Substrate (mM) | Reaction Time (hr) | Yield (mM) | Optical Purity (D-Form) (% ee) |
|---|---|---|---|---|
| 4-Hydroxybenzaldehyde + prussic acid | 4 | 17 | 3.5 (88%) | 100 |
| 4-Methylbenzaldehyde + prussic acid | 4 | 17 | 3.7 (93%) | 100 |
| 4-Methoxybenzaldehyde + prussic acid | 3 | 17 | 2.5 (83%) | 100 |

While the invention has been described in detail and with reference to specific examples thereof, it will be apparent to one skilled in the art that various changes and modifications can be made therein without departing from the spirit and scope thereof.

What is claimed is:

1. A process for producing an optically active α-hydroxycarboxylic acid having a phenyl group of formula (I):

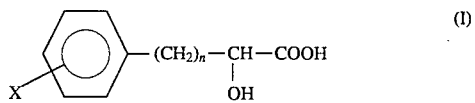
(I)

wherein X represents a hydrogen atom, a hydroxyl group, an aliphatic saturated alkyl group having from 1 to 3 carbon atoms, an aliphatic saturated alkoxy group having from 1 to 3 carbon atoms, a thioalkyl group, a halogen atom, a phenyl group, a phenoxy group, an amino group or a nitro group, which is bonded to the o-, m-, or p-position; and n represents 0, 1, or 2, which comprises contacting a racemic α-hydroxynitrile of formula (II):

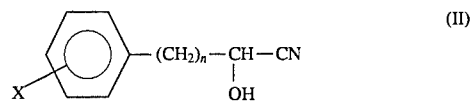
(II)

wherein X and n are as defined above, or a mixture of an aldehyde corresponding to said nitrile and prussic acid, in a neutral to basic aqueous medium, with a microorganism or treated cells thereof, wherein the microorganism is *Gordona terrae*, and recovering the optically active α-hydroxycarboxylic acid having a phenyl group of formula (I).

2. The process as claimed in claim 1, wherein said microorganism is *Gordona terrae* MA-1 (FERM BP-4535).

3. The process as claimed in claim 1, wherein said α-hydroxynitrile is a member selected from the group consisting of mandelonitrile, 2-chloromandelonitrile, 3-chloromandelonitrile, 4-chloromandelonitrile, 4-hydroxymandelonitrile, 4-methylmandelonitrile, 4-methoxymandelonitrile, 4-methylthiomandelonitrile, 4-aminomandelonitrile, 4-nitromandelonitrile, 3-phenoxymandelonitrile, phenyllactonitrile, 4-phenyl-α-hydroxybutyronitrile, 3-(2-methoxyphenyl)-lactonitrile, 3-(3-methoxyphenyl)-lactonitrile, 3-(4-methoxyphenyl)-lactonitrile, 4-(4-fluorophenyl)-α-hydroxybutyronitrile, 4-(2-chlorophenyl)-α-hydroxybutyronitrile, 4-(4-bromophenyl)-α-hydroxybutyronitrile, 4-(2-trifluoromethylphenyl)-α-hydroxybutyronitrile, 4-(3-trifluoromethylphenyl)-α-hydroxybutyronitrile and 4-(2-hydroxyphenyl)-α-hydroxybutyronitrile.

4. The process as claimed in claim 1, wherein the reaction occurs in a system having a pH of 4 to 11.

5. The process as claimed in claim 1, wherein the yield of the compound of formula (I) in the reaction is 50 to 100% based on the amount of the α-hydroxynitrile of formula (II).

6. The process as claimed in claim 1, wherein the reaction occurs in the presence of a member selected from the group consisting of sodium sulfite, acid sodium sulfite, sodium dithionite, potassium sulfite, acid potassium sulfite, potassium dithionite, ammonium sulfite, acid ammonium sulfite, and ammonium dithionite.

* * * * *